(12) United States Patent
Hull et al.

(10) Patent No.: US 10,238,449 B2
(45) Date of Patent: Mar. 26, 2019

(54) SYSTEMS AND METHODS FOR PERCUTANEOUS INTRAVASCULAR ACCESS FOR ARTERIOVENOUS FISTULA

(71) Applicant: Avenu Medical, Inc., San Juan Capistrano, CA (US)

(72) Inventors: Jeffrey E. Hull, Midlothian, VA (US); Mark A. Ritchart, Dana Point, CA (US)

(73) Assignee: Avenu Medical, Inc., San Juan Capistrano, CA (US)

( * ) Notice: Subject to any disclaimer, the term of this patent is extended or adjusted under 35 U.S.C. 154(b) by 0 days.

(21) Appl. No.: 14/944,090

(22) Filed: Nov. 17, 2015

(65) Prior Publication Data

US 2016/0135873 A1    May 19, 2016

Related U.S. Application Data

(62) Division of application No. 13/956,221, filed on Jul. 31, 2013.

(Continued)

(51) Int. Cl.
*A61B 18/14*    (2006.01)
*A61B 18/08*    (2006.01)
(Continued)

(52) U.S. Cl.
CPC ........ *A61B 18/1445* (2013.01); *A61B 18/085* (2013.01); *A61B 18/148* (2013.01);
(Continued)

(58) Field of Classification Search
CPC ........................ A61B 18/1442; A61B 18/1445
See application file for complete search history.

(56) References Cited

U.S. PATENT DOCUMENTS 4,251,310 A    2/1981   Goldhaber et al.
5,571,136 A *  11/1996  Weaver .................. A61B 10/04
                                                    606/174

(Continued)

FOREIGN PATENT DOCUMENTS

JP    2002011019 A    1/2002
WO       0149187 A1   7/2001

OTHER PUBLICATIONS

International Search Report and Written Opinion in related PCT Application US2013/053070. International Filing date Jul. 31, 2013.

(Continued)

*Primary Examiner* — Ronald Hupczey, Jr.
*Assistant Examiner* — Bo Ouyang
(74) *Attorney, Agent, or Firm* — Donald E. Stout; Stout, Usa & Buyan, LLP

(57) ABSTRACT

A device for extending, elongating, or repairing a previously created arteriovenous fistula between a first blood vessel and an adjacent second blood vessel includes a main body having a primary lumen and an articulating jaw member disposed at the distal end of the main body. The jaw member is configured with two elements to allow rotation of one element about a pivot point to grasp tissue while being rotated. The jaw member is also configured to allow thermal energy delivery to one or both elements of the jaw member that allow tissue welding and cutting. A second lumen located within one element of the jaw member is configured to allow advancement over a guidewire into the second vessel while the other element of the jaw member remains within the first blood vessel at the position where the arteriovenous fistula, or aperture, exists between the first and second blood vessel.

12 Claims, 6 Drawing Sheets

Related U.S. Application Data

(60) Provisional application No. 61/678,240, filed on Aug. 1, 2012.

(51) Int. Cl.
*A61B 18/24* (2006.01)
*A61B 18/00* (2006.01)

(52) U.S. Cl.
CPC .......... *A61B 18/1492* (2013.01); *A61B 18/24* (2013.01); *A61B 2018/00404* (2013.01); *A61B 2018/00601* (2013.01); *A61B 2018/00619* (2013.01); *A61B 2018/00982* (2013.01); *A61B 2018/146* (2013.01)

(56) References Cited

U.S. PATENT DOCUMENTS

| | | |
|---|---|---|
| 5,626,608 A | 5/1997 | Cuny et al. |
| 6,139,508 A | 10/2000 | Simpson et al. |
| 6,361,540 B1 | 3/2002 | Gauderer |
| 6,394,964 B1 | 5/2002 | Sievert, Jr. et al. |
| 6,443,973 B1 | 9/2002 | Whitman |
| 7,875,029 B1 | 1/2011 | Hausen |
| 7,892,208 B2 | 2/2011 | Schnell et al. |
| 2003/0100920 A1* | 5/2003 | Akin ............... A61B 17/11 606/213 |
| 2004/0116901 A1 | 6/2004 | Appling |
| 2005/0143763 A1 | 6/2005 | Ortiz |
| 2005/0277952 A1 | 12/2005 | Arp et al. |
| 2006/0217706 A1* | 9/2006 | Lau ................ A61B 17/29 606/45 |
| 2008/0051626 A1* | 2/2008 | Sato ............... A61B 1/00082 600/101 |
| 2009/0023985 A1 | 1/2009 | Ewers |
| 2009/0234355 A1 | 9/2009 | Edwards |
| 2010/0324446 A1 | 12/2010 | Pendleton |
| 2011/0152759 A1* | 6/2011 | Clymer ........... A61B 10/0283 604/93.01 |
| 2012/0059371 A1 | 3/2012 | Anderson et al. |
| 2012/0065652 A1* | 3/2012 | Cully ............. A61B 17/11 606/153 |
| 2012/0116426 A1* | 5/2012 | Swain ............. A61B 17/08 606/153 |
| 2012/0265132 A1* | 10/2012 | Nomura .......... A61B 1/00098 604/95.04 |

OTHER PUBLICATIONS

Extended European Search Report dated Apr. 4, 2016 in connection with corresponding European App. No. 13824823.2.

\* cited by examiner

SYSTEMS AND METHODS FOR PERCUTANEOUS INTRAVASCULAR ACCESS FOR ARTERIOVENOUS FISTULA

This application is a divisional application under 35 U.S.C. 120 of U.S. application Ser. No. 13/956,221, entitled Systems and Methods for Percutaneous Intravascular Access for Arteriovenous Fistula, filed on Jul. 31, 2013 and presently pending, which in turn claims the benefit under 35 U.S.C. 119(e) of the filing date of Provisional U.S. Application Ser. No. 61/678,240, entitled Systems and Methods for Percutaneous Intravascular Access for Arteriovenous Fistula, filed on Aug. 1, 2012, which applications are each herein expressly incorporated herein by reference, in their entirety.

BACKGROUND OF THE INVENTION

In the body, various fluids are transported through conduits throughout the organism to perform various essential functions. Blood vessels, arteries, veins, and capillaries carry blood throughout the body, carrying nutrients and waste products to different organs and tissues for processing. Bile ducts carry bile from the liver to the duodenum. Ureters carry urine from the kidneys to the bladder. The intestines carry nutrients and waste products from the mouth to the anus.

In medical practice, there is often a need to connect conduits to one another or to a replacement conduit to treat disease or dysfunction of the existing conduits. The connection created between conduits is called an anastomosis.

In blood vessels, anastomoses are made between veins and arteries, arteries and arteries, or veins and veins. The purpose of these connections is to create either a high flow connection, or fistula, between an artery and a vein, or to carry blood around an obstruction in a replacement conduit, or bypass. The conduit for a bypass is a vein, artery, or prosthetic graft.

An anastomosis is created during surgery by bringing two vessels or a conduit into direct contact, and to create a leak-free blood flow path between them. The vessels are joined together with suture or clips, in an open surgical procedure. The anastomosis can be end-to-end, end-to-side, or side-to-side. In blood vessels, the anastomosis is elliptical in shape and is most commonly sewn by hand with a continuous suture. Other methods for anastomosis creation have been used including carbon dioxide laser, and a number of methods using various connecting prosthesis, clips, and stents. Such procedures are time consuming, clinician dependent (open to surgical error), and often result in strictures, or clotting of the vein or artery.

An arterio-venous fistula (AVF) is created by connecting an artery to a vein. This type of connection is used for hemodialysis, to increase exercise tolerance, to keep an artery or vein open, or to provide reliable access for chemotherapy.

An alternative is to connect a prosthetic graft from an artery to a vein for the same purpose of creating a high flow connection between artery and vein. This is called an arterio-venous graft, and requires two anastomoses. One is between artery and graft, and the second is between graft and vein.

A bypass is similar to an arteriovenous graft. To bypass an obstruction, two anastomoses and a conduit are required. A proximal anastomosis is created from a blood vessel to a conduit. The conduit extends around the obstruction, and a second distal anastomosis is created between the conduit and vessel beyond the obstruction.

As noted above, in current medical practice, it is desirable to connect arteries to veins to create a fistula for the purpose of hemodialysis. The process of hemodialysis requires the removal of blood from the body at a rapid rate, passing the blood through a dialysis machine, and returning the blood to the body. The access to the blood circulation is achieved with catheters placed in large veins, prosthetic grafts attached to an artery and a vein, or a fistula where an artery is attached directly to the vein.

Fistulas for hemodialysis are required by patients with kidney failure. The fistula provides a high flow of blood that can be withdrawn from the body into a dialysis machine to remove waste products and then returned to the body. The blood is withdrawn through a large access needle near the artery and returned to the fistula through a second large return needle. These fistulas are typically created in the forearm, upper arm, less frequently in the thigh, and in rare cases, elsewhere in the body. It is important that the fistula be able to achieve a flow rate of 500 ml per minute or greater. Dialysis fistulas have to be close to the skin (<6 mm), and large enough (>4 mm) to access with a large needle. The fistula needs to be long enough (>6 cm) to allow adequate separation of the access and return needle to prevent recirculation of dialysed and non-dialysed blood between the needles inserted in the fistula.

Fistulas are created in anesthetized patients by carefully dissecting an artery and vein from their surrounding tissue, and sewing the vessels together with fine suture or clips. The connection thus created is an anastomosis. It is highly desirable to be able to make the anastomosis quickly, reliably, with less dissection, and with less pain. It is important that the anastomosis is the correct size, is smooth, and that the artery and vein are not twisted.

SUMMARY OF THE INVENTION

The present invention comprises a device to allow extension, elongation or repair of a previously created arteriovenous fistula between a first blood vessel and an adjacent second blood vessel which comprises a main body having a primary lumen and an articulating jaw member disposed at the distal end of the main body and configured with two elements to allow rotation of one element about a pivot point to grasp tissue while being rotated. The jaw member is also configured to allow thermal energy delivery to one or both elements of the jaw member that allow tissue welding and cutting with DC, RF, Laser or Ultrasonic energy. A second lumen located within one element of the jaw member is configured to allow advancement over a guidewire into the second vessel while the other element of the jaw member remains within the first blood vessel at the position where the arteriovenous fistula, or aperture, exists between the first and second blood vessel.

In one embodiment, the articulating jaw member is configured to allow rotation of both elements about a pivot point to grasp tissue and apply thermal energy.

In another aspect of the invention, a method of elongation of the passage between adjacent first and second blood vessels comprises a step of positioning a main body of the device within the first vessel and advancing one element of the jaw member through the aperture between the vessels, and into the second vessel, so that the jaw element is disposed within the second vessel. The articulating element is actuated to rotate about the pivot point of the jaw member for grasping and compressing tissue adjacent to the aperture between the first blood vessel and the adjacent second blood vessel.

The method further comprises the step of applying thermal energy to one or both elements of the jaw member to cut an extension to the aperture and weld the adjacent first and second blood vessel using DC, RF, Laser or ultrasonic energy.

More particularly, there is provided in one aspect of the invention a device for elongating, extending, or repairing a tissue aperture, which comprises a handle, a body connected to and extending distally from the handle, comprised of a flexible material and having a primary lumen, a rigid jaw member connected to and extending distally from the flexible body, and a tissue cutting element disposed on the jaw member. Preferably, the flexible material comprising the body is a polymer having a Shore A hardness of 70-90. The rigid jaw member is preferably fabricated of a rigid material comprising either a metal or a rigid polymer having a Shore A hardness greater than 90, though, of course, other equivalent materials may be utilized alternatively, in both instances.

The jaw member comprises two elements, each having distal ends, wherein one of the elements is pivotable relative to the other element to create a spacing of varying sizes between the two elements at their respective distal ends. In one of the disclosed embodiments, one of the elements is a stationary element and the other element is an articulating element, the articulating element being pivotable about a pivot point disposed on a proximal end thereof. In another disclosed alternative embodiment, both of the elements are articulating elements.

In the disclosed embodiments, the tissue cutting element comprises an electrode for energizing the tissue to be cut. Two electrodes are illustrated in the drawings. A power supply and an activation switch are disposed on the handle for activating the electrode(s). The supplied energy may be thermal energy, RF energy, laser energy, ultrasonic energy, or the like.

A lever is provided on the handle for moving at least one of the jaw member elements relative to the other one to increase or decrease the spacing between the distal ends of the elements, thereby opening or closing the jaws of the jaw member. As disclosed, a wire connects the lever to the jaw member for opening or closing the jaw member. A ratcheting mechanism is provided on the lever for applying variable incremental pressure to the jaw member.

A conductor connects the power supply and activation switch to the electrode. The electrode may be comprised of aluminum or other suitable conductive material. A secondary lumen is disposed in one of the jaw elements.

The jaw member has a closed orientation wherein both jaw elements are substantially aligned with a longitudinal axis of the primary lumen, and open orientations wherein at least one of the jaw elements is disposed at a substantial angle of varying sizes from the longitudinal axis of the primary lumen.

In another aspect of the invention, there is disclosed a method of extending, elongating, or repairing a fistula between adjacent first and second vessels. The method comprises a step of inserting a main body of a device into the first vessel so that a distal end thereof lies within a blood flow passage of the first vessel. A jaw member disposed at a distal end of the main body is opened, and the open jaw member is disposed so that a portion of tissue adjacent to the fistula is disposed between elements thereof. The elements of the jaw member are closed to clamp the portion of tissue therebetween. An electrode on the jaw member is energized to cut and weld the tissue to extend the fistula. The device is then withdrawn from the site.

The inserting step may further comprise a step of aligning a lumen in the main body over a guidewire, and sliding the device over the guidewire to the desired location. The energizing step may comprise applying thermal energy of about 10-50 watts to the clamped tissue. During the energizing step, the tissue temperature is increased to about 100-400 degrees C. to cut and weld an extended aperture of about 1-5 mm from the primary blood vessel to the secondary blood vessel. Imaging guidance is preferably used to insert the device into a procedural site and monitor the cutting and welding step.

The invention, together with additional features and advantages thereof, may best be understood by reference to the following description taken in conjunction with the accompanying illustrative drawings.

DESCRIPTION OF THE PREFERRED EMBODIMENT

Figure 1:
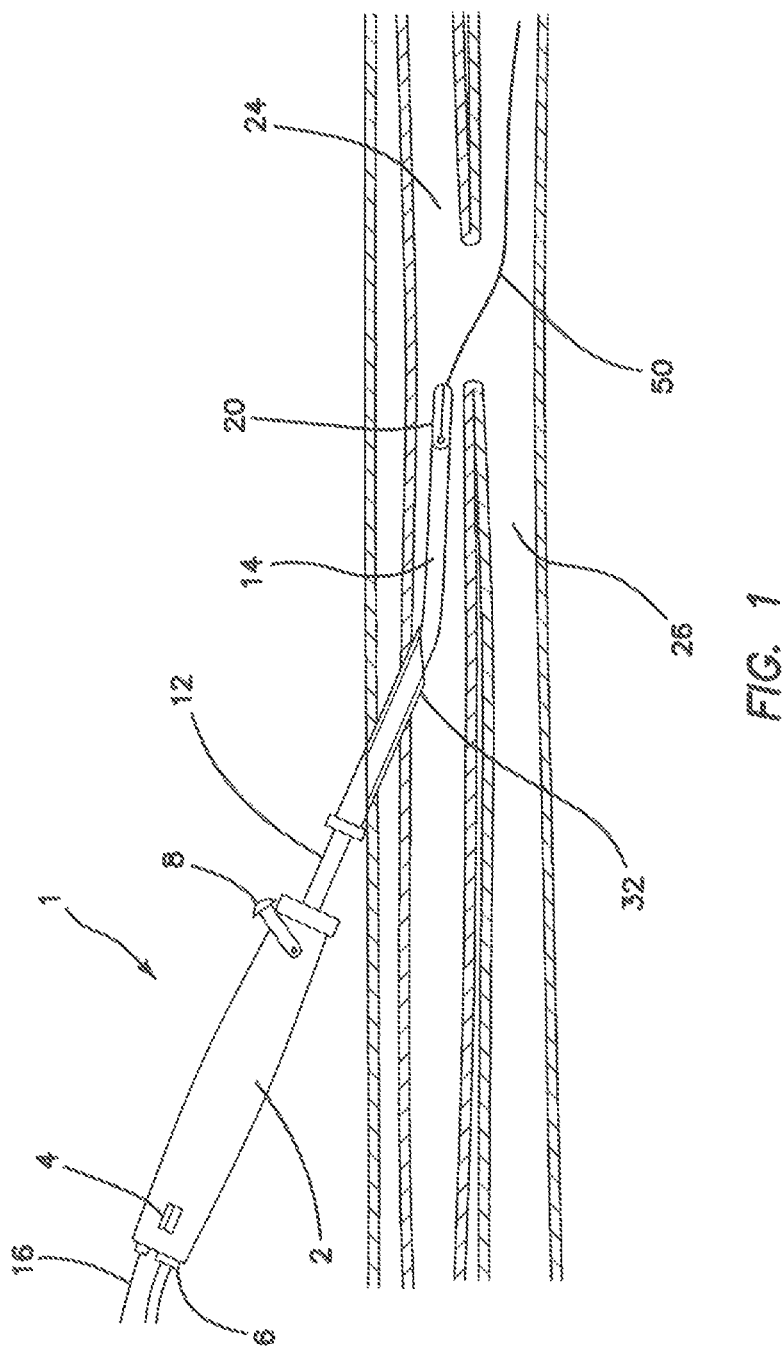
FIG. 1 is a view of one embodiment of the device of the present invention, wherein the device has been percutaneously or surgically positioned at a desired location in a blood vessel near the arteriovenous fistula.
Figure 2:
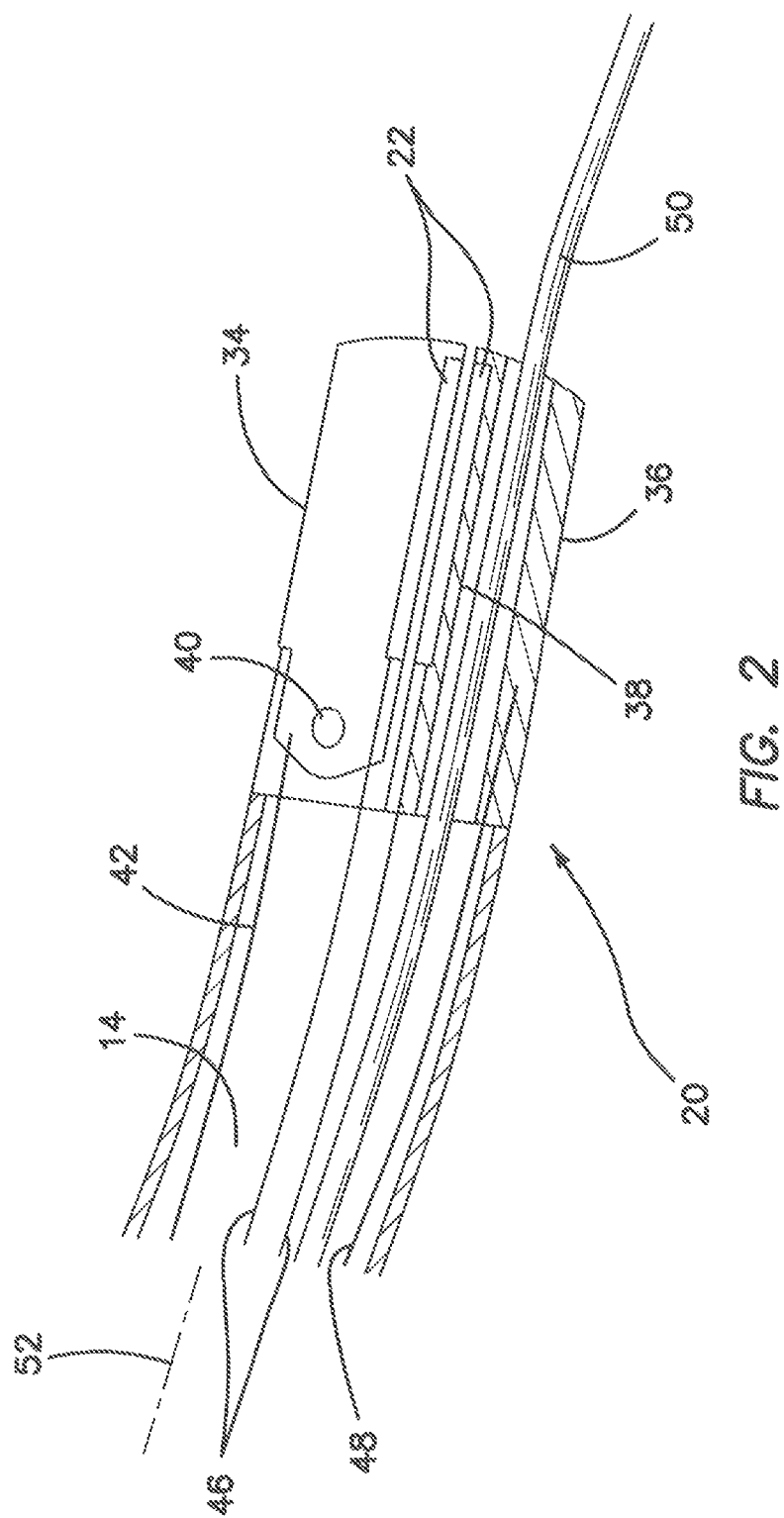
FIG. 2 is a view illustrating the distal jaw member in isolation.
Figure 3:
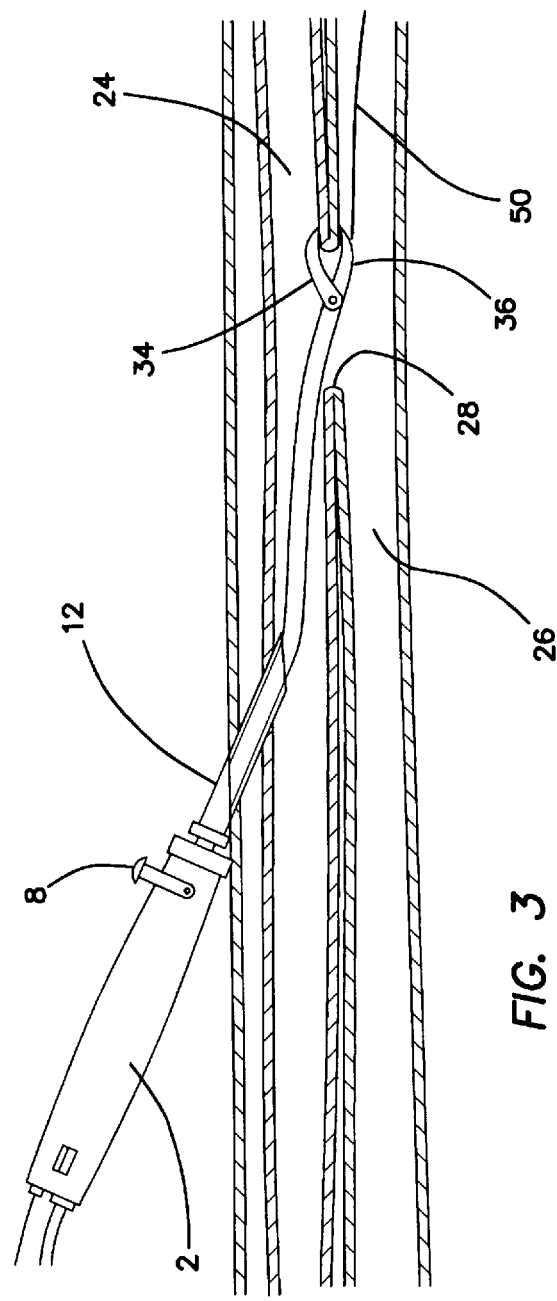
FIG. 3 is a view similar to FIG. 1, wherein one element of the jaw member illustrated in FIG. 2 has been advanced over the guidewire into the second blood vessel while the second element has been articulated to the open position within the first blood vessel.

Referring now more particularly to the drawings, one embodiment of a device constructed in accordance with the principles of the present invention is shown. As illustrated in FIGS. 1 and 2, a device 1 comprises a handle 2 with an activation switch 4, an electrical connector 6, and a jaw lever 8. A 4-7 F (French) flexible (70-90 Shore A) polymer main body 12, having a primary lumen 14 and rigid distal jaw member 20, is provided. The main body is attached to the handle 2 at the proximal end and the jaw member 20 at the distal end. The electrical connector 6 allows connection to temperature display and power supply devices for temperature feedback and DC thermal energy delivery, though other modalities such as Radio Frequency (RF) or laser are can be employed. Lever 8 is constructed with a ratcheting mechanism to allow variable incremental pressure (approximately 100 mN/mm$^2$-500 mN/mm$^2$) to electrodes 22 on jaw member 20 (FIG. 2) as desired by the practitioner. To begin the inventive method of intravascular arteriovenous fistula extension or elongation, the practitioner selects an appropriate procedural site having each of a first blood vessel 24 and a second blood vessel 26 in close proximity to one another and having a previously created arteriovenous fistula 28 disposed therebetween (FIG. 3). In currently preferred approaches, the first blood vessel 24 comprises a vein, and the second blood vessel 26 comprises an artery, but the invention is not limited to this arrangement. Under real time imaging guidance such as ultrasound or fluoroscopy, the main body 12 is inserted into the first vessel 24 so that a distal end 32 thereof lies within the blood flow passage of the first vessel. Preferably, this insertion step is performed using percutaneous technique, but open surgery and direct visualization may also be employed.

With reference now particularly to FIG. 2, the jaw member 20 comprises an articulating element 34 and a stationary element 36, including a secondary lumen 38. The articulating element 34 is movable about a pivot point 40, and is attached to a tendon wire 42, as illustrated. It should be noted that the invention is not limited to a single articulating element 34, pivot point 40, and tendon wire 42, though only one of each is shown in this particular embodiment. Articulating element 34 and stationary element 36 are preferably constructed of a rigid material such as metal or rigid (>90 Shore A) polymer, with 1-5 mm elongate electrodes 44 attached to the opposing surfaces. Electrodes 44, preferably constructed of an electrically and thermally conductive material, such as aluminum, are attached to the electrical connector 6 on handle 2 via conductors 46, which are preferably constructed of an electrically and thermally conductive material such as copper. A temperature sensor 48, such as a thermocouple or thermistor, is attached to the stationary element 36 on one end and the electrical connector 6 on the opposite end. Tendon wire 42, preferably constructed of 18-24 Ga (Gauge) wire, is attached to the articulating element 34 on one end and to the jaw lever 8 on the other end. Stationary element 36 includes the secondary lumen 38, as noted above. These elements, including the primary lumen 14 of the main body shaft 12, provide an externally communicating passage to allow advancement of the device 1 over a guidewire 50.

Referring now particularly to FIGS. 2 and 3, the orientation of the articulating element 34 of the jaw member 20 can be rotationally adjustable between a range of rotation about the pivot point 40. A first, or closed, position is illustrated in FIG. 2 where the articulating element 34 is substantially aligned with the longitudinal axis 52 of the primary lumen 14 and the secondary lumen 38. As will be described more fully below, the closed orientation is utilized during the initial device insertion steps, as well as the device withdrawal steps, while variable rotated orientations are the operative for creating the extension or elongation of the arteriovenous fistula 28. This variable orientation may be desirable by the practitioner to incrementally adjust the opening of the jaw member 20 to achieve an optimal size extension of the aperture 28 between primary vessel 24 and secondary vessel 26.

Referring again to FIG. 3, once the main body 12 is inserted into the first vessel 24 and advanced to the desired site determined by the practitioner using ultrasound or fluoroscopic imaging, as previously described, it may be desired to adjust the rotation of the articulating element 34 to increase the angle of the opening of jaw member 20, by rotating the lever 8 of main body handle 2. Since the jaw member 20 is configured to have echogenic and radiopaque properties to allow the practitioner to visualize the orientation under real time imaging guidance, this will allow the practitioner to more effectively adjust the opening of jaw member 20 through direct visualization as it is advanced into the desired position in the arteriovenous fistula aperture 28 between the primary blood vessel 24 and the secondary blood vessel 26 to achieve the desired length of extension of the aperture. This step may be repeated as desired by the practitioner rotating lever 8 of main body handle 2 to adjust the open position of articulating element 34, until the desired arteriovenous fistula aperture extension has been achieved.

Figure 4:
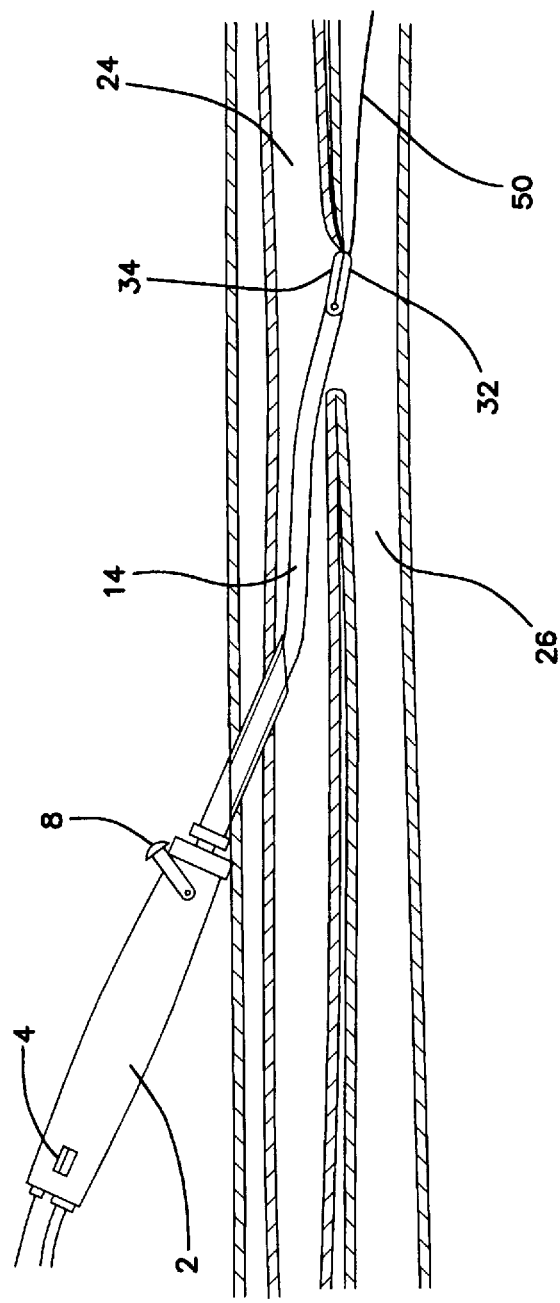
FIG. 4 is a view similar to FIG. 3, wherein the second element of the jaw member is articulated from the open to closed position to grasp tissue and cut and weld an extension to the arteriovenous fistula aperture.

With reference now to FIG. 4, once the practitioner has oriented the stationary element 36 of the jaw member 20 as desired through the arteriovenous fistula aperture 28 and within secondary blood vessel 26, the lever 8 of the handle 2 is rotated to the fully closed position to compress the blood vessels within the jaw member 20. Activation switch 4 is activated to deliver thermal energy of between about 10-50 W to the jaws 20, sufficient to raise the tissue temperature to about 100-400 degrees C. to cut and weld an extended aperture 28 of 1-5 mm from the primary blood vessel 24 to the secondary blood vessel 26. This may be done under direct imaging guidance to verify energy delivery in the area desired by the practitioner, due to the creation of micro bubbles visible under transcutaneous ultrasound in the area of direct thermal energy. The practitioner may also verify acceptable extension of the aperture through direct visualization of the larger opening in the aperture under imaging guidance.

Figure 5:
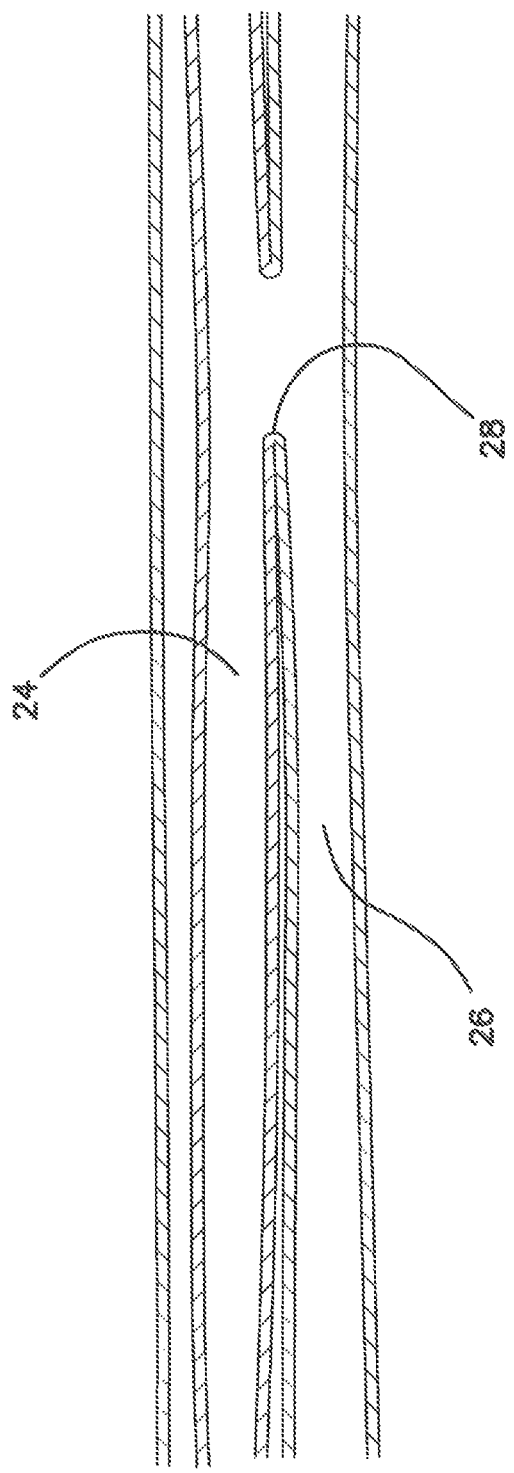
FIG. 5 illustrates the extended communicating aperture created by the device and methods of the present invention after the inventive device of FIGS. 1-4 has been withdrawn from the procedural site.

With reference now to FIG. 5, once the extension of arteriovenous fistula aperture 28 from primary blood vessel 24 to secondary blood vessel 26 has been achieved as previously described, the practitioner withdraws device 1 completely from the body, thus leaving an extended aperture 28 in the anastomosis between the primary vessel 24 and the secondary vessel 26.

Figure 6:
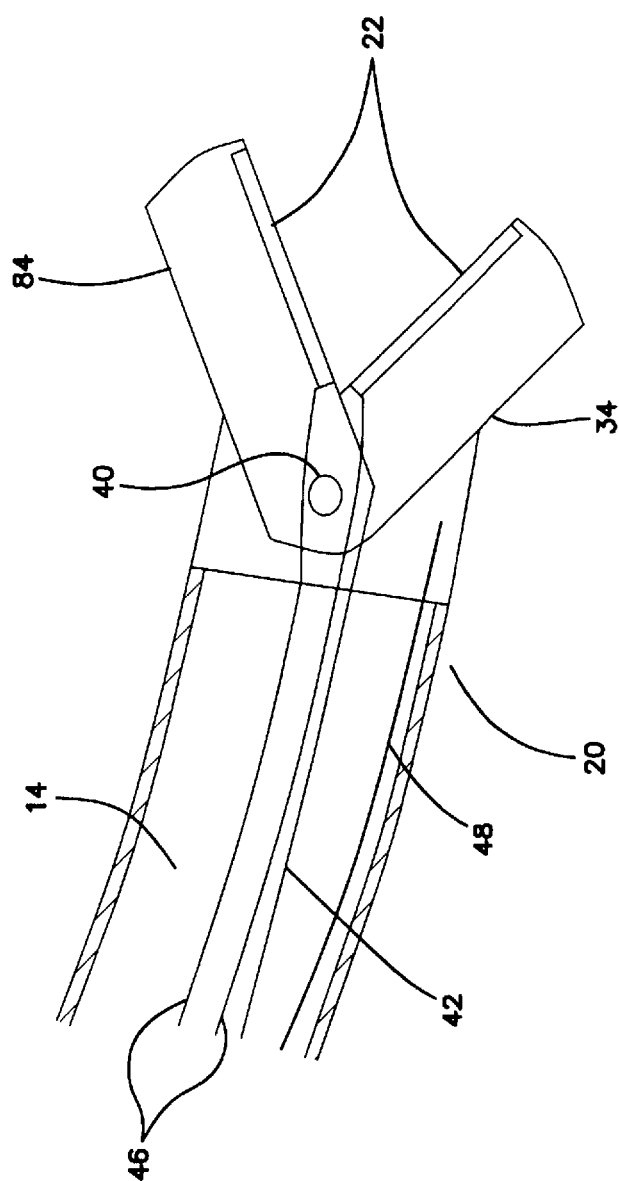
FIG. 6 illustrates an alternate embodiment of the distal jaw member.

FIG. 6 illustrates a detail view of an alternate embodiment of jaw member 20 that is configured with two articulating elements 34, rather than a stationary element and an articulating element, as in the embodiment of FIGS. 1-5. As is evident to those skilled in the art, an advantage of this embodiment is the ability to open the jaws 34 to a substantially wider extent than is the case with the first embodiment. In all other respects, the embodiment of FIG. 6 is utilized in the same manner as is the embodiment of FIGS. 1-5.

What is claimed is:
1. A method of extending, elongating, or repairing a fistula between adjacent first and second blood vessels, comprising:
    inserting a main body of a device into the first blood vessel so that a distal end thereof lies within a blood flow passage of the first blood vessel, the distal end of the main body having a jaw member comprising a first jaw element and a second jaw element disposed in a closed orientation relative to one another;
    opening the jaw member by moving the first jaw element relative to the second jaw element about a pivot point, thereby increasing a spacing between the first jaw element and the second jaw element;
    disposing the open jaw member within the fistula and at an edge thereof so that a portion of tissue adjacent to and defining the fistula, comprised of portions of the walls of each of the first and second blood vessels, is disposed between the first and second jaw elements;
    closing the first and second elements of the jaw member, by moving the first jaw element relative to the second jaw element about the pivot point, to clamp the portion of tissue therebetween;
    energizing an electrode on said jaw member to cut and weld the tissue to extend the fistula; and
    withdrawing the entire device, including both the main body and the jaw member, from the fistula site.

2. The method as recited in claim 1, wherein the inserting step comprises aligning a lumen in the device over a guidewire, and sliding the device over said guidewire to the desired location.

3. The method as recited in claim 1, wherein the energizing step comprises using the electrode disposed on the jaw member to apply thermal energy of 10-50 watts to the clamped tissue.

4. The method as recited in claim 3, wherein the tissue temperature is increased to 100-400 degrees C. to cut and weld an extended aperture of 1-5 mm from the primary blood vessel to the secondary blood vessel.

5. The method as recited in claim 4, wherein the tissue temperature is sensed by a temperature sensor disposed on the jaw member.

6. The method as recited in claim 1, wherein imaging guidance is used to insert the device into a procedural site and monitor the cutting and welding step.

7. The method as recited in claim 6, wherein the imaging guidance is obtained from one of an ultrasound and a fluoroscopy system.

8. The method as recited in claim 1, wherein the inserting step is performed percutaneously.

9. The method as recited in claim 1, wherein the first blood vessel is a vein and the second blood vessel is an artery.

10. The method as recited in claim 1, wherein the second jaw element remains stationary during each of the opening and the closing steps.

11. The method as recited in claim 1, wherein the second jaw element and the first jaw element both move relative to one another during each of the opening and the closing steps.

12. The method as recited in claim 1, wherein the opening and closing steps are each performed by actuation of a jaw lever on a handle of the main body, wherein actuation of the jaw lever moves a tendon wire to actuate one or both of the first and second jaw elements.

* * * * *